(12) United States Patent
Henderson et al.

(10) Patent No.: US 9,342,658 B2
(45) Date of Patent: *May 17, 2016

(54) DYNAMIC REFILL LEVEL FOR MEDICATION DISPENSING APPARATUS

(71) Applicant: CERNER INNOVATION, INC., Kansas City, KS (US)

(72) Inventors: Todd Reed Henderson, Leawood, KS (US); Mark David Gromowsky, Kansas City, MO (US)

(73) Assignee: CERNER INNOVATION, INC., Kansas City, KS (US)

( * ) Notice: Subject to any disclaimer, the term of this patent is extended or adjusted under 35 U.S.C. 154(b) by 86 days.

This patent is subject to a terminal disclaimer.

(21) Appl. No.: 14/143,302

(22) Filed: Dec. 30, 2013

(65) Prior Publication Data

US 2014/0114474 A1    Apr. 24, 2014

Related U.S. Application Data

(63) Continuation of application No. 13/169,583, filed on Jun. 27, 2011, now Pat. No. 8,670,864.

(51) Int. Cl.
*G06Q 20/00* (2012.01)
*G06F 19/00* (2011.01)

(52) U.S. Cl.
CPC ........ *G06F 19/3456* (2013.01); *G06F 19/3462* (2013.01)

(58) Field of Classification Search
CPC .. G06F 19/3462; G06F 19/3456; G06Q 50/22
USPC ................ 705/2; 700/236, 241, 244, 237
See application file for complete search history.

(56) References Cited

U.S. PATENT DOCUMENTS

| 7,978,564 | B2 * | 7/2011 | De La Huerga | .. A61M 5/14212 700/242 |
| 8,670,864 | B2 * | 3/2014 | Henderson | .......... G06F 19/3462 700/236 |
| 2010/0082458 | A1 * | 4/2010 | Godlewski | ......... G06Q 30/0635 705/28 |

* cited by examiner

*Primary Examiner* — Timothy Waggoner
(74) *Attorney, Agent, or Firm* — Shook, Hardy & Bacon L.L.P.

(57) ABSTRACT

A dynamic refill level is used for determining medication refill requirements for a medication at a medication dispensing apparatus. A quantity of medication likely needed from the medication dispensing apparatus until a next scheduled refill is determined. A dynamic refill level is set for the medication based on the quantity of medication likely needed. A current count for the medication in the medication dispensing apparatus is compared against the dynamic refill level. If the current count satisfies the dynamic refill level, there is no need to refill the medication. However, if the current count does not satisfy the dynamic refill level, there is a need to refill the medication.

20 Claims, 6 Drawing Sheets

SELECT A ROW ON THE LEFT TO SEE DETAILS.
STOCK                    BROMANYL 12.5 MG-10MG/5 ML SYR

REFILL < 20
☐ ENABLE DYNAMIC REFILL?              BUFFER LEVEL:    [        ]
REFILL LEVEL:            [ 8    ]     MAXIMUM LEVEL:   [ 20     ]
                         CRITICAL ≤ 8          INCREMENTS ≤ 20
CRITICAL LEVEL:          [ 5    ]     IN INCREMENTS OF: [ 5     ]
COUNT REQUIREMENT:       [ CONFIRM                              ▼]
PACKAGE TYPE:            [ ML                                   ▼]
COST CENTER:             [                                      ▼]
SUB ACCOUNT:             [                                      ▼]
OVERRIDE LEVEL:          [ LEVEL 01                             ▼]
☐ PREVENT CHANGES

[ SAVE ] [ UNASSIGN ] [ CANCEL ]

*FIG. 3A.*

SELECT A ROW ON THE LEFT TO SEE DETAILS.
STOCK                    BROMANYL 12.5 MG-10MG/5 ML SYR

REFILL < 20
☑ ENABLE DYNAMIC REFILL?              BUFFER LEVEL:    [ 25%    ]
REFILL LEVEL:            [ 8    ]     MAXIMUM LEVEL:   [ 20     ]
                         CRITICAL ≤ 8          INCREMENTS ≤ 20
CRITICAL LEVEL:          [ 5    ]     IN INCREMENTS OF: [ 1     ]
COUNT REQUIREMENT:       [ CONFIRM                              ▼]
PACKAGE TYPE:            [ ML                                   ▼]
COST CENTER:             [                                      ▼]
SUB ACCOUNT:             [                                      ▼]
OVERRIDE LEVEL:          [ LEVEL 01                             ▼]
☐ PREVENT CHANGES

[ SAVE ] [ UNASSIGN ] [ CANCEL ]

*FIG. 3B.*

DYNAMIC REFILL LEVEL FOR MEDICATION DISPENSING APPARATUS

CROSS-REFERENCE TO RELATED APPLICATIONS

This application is a continuation of U.S. patent application Ser. No. 13/169,583, filed Jun. 27, 2011, the entire disclosure of which is hereby incorporated by reference.

BACKGROUND

Many hospitals include a hospital pharmacy department that is responsible for dispensing medications to patients in various areas of the hospitals. In some hospitals, the medications are dispensed in a distributed environment with a central pharmacy (or multiple "central" pharmacies) and a number of medication dispensing apparatuses remotely situated in various locations throughout the hospital. The remotely-located medication dispensing apparatuses allow medications to be stored and dispensed closer to the location of patient care, which may provide a number of benefits, including both simplifying and speeding up the process of clinicians obtaining medications for their patients.

Among other things, a hospital pharmacy department may be responsible for tracking the medications stored and dispensed by the various medication dispensing apparatuses throughout a hospital. This may include identifying when medication refills are required at each medication dispensing apparatus and sending personnel to refill each medication dispensing apparatus with medications. There are often a number of inefficiencies in how hospital pharmacies typically handle the refilling process for medication dispensing apparatuses, including refilling medication dispensing apparatuses with medications when not required to meet medication-dispensing needs. This results in a number of problems, including additional and unnecessary work for pharmacy personnel and storing costly medications when those medications are not needed.

BRIEF SUMMARY

Embodiments of the present invention relate to employing a dynamic refill level for a medication dispensing apparatus. A quantity of medication likely needed from the medication dispensing apparatus until a next scheduled refill is determined. A dynamic refill level is set for the medication based on the quantity of medication likely needed. A current count for the medication in the medication dispensing apparatus is compared against the dynamic refill level. If the current count satisfies the dynamic refill level, there is no need to refill the medication. However, if the current count does not satisfy the dynamic refill level, there is a need to refill the medication.

Accordingly, in one aspect, an embodiment of the present invention is directed to one or more computer storage media storing computer-useable instructions that, when used by one or more computing devices, cause the one or more computing devices to perform operations. The operations include estimating a quantity of a medication likely needed from a medication dispensing apparatus during a time period until a next scheduled medication refill for the medication dispensing apparatus, the next scheduled medication refill occurring in accordance with a scheduled basis for refilling the medication dispensing apparatus with a plurality of medications. The operations also include setting a dynamic refill level for the medication based on the quantity of the medication predicted as likely needed, the dynamic refill level for determining whether to refill the medication during a current scheduled medication refill for the medication dispensing apparatus occurring in accordance with the scheduled basis for refilling the medication dispensing apparatus.

In another embodiment, an aspect of the invention is directed to one or more computer storage media storing computer-useable instructions that, when used by one or more computing devices, cause the one or more computing devices to perform operations. The operations include determining a dynamic refill level for a medication at a medication dispensing apparatus for a current scheduled medication refill occurring in accordance with a scheduled basis for refilling the medication dispensing apparatus with a plurality of medications, the dynamic refill level being determined by: predicting a quantity of the medication likely needed from the medication dispensing apparatus during a time period until a next scheduled medication refill for the medication dispensing apparatus, the next scheduled medication refill occurring in accordance with the scheduled basis for refilling the medication dispensing apparatus, and setting the dynamic refill level for the medication based on the quantity of the medication predicted as likely needed. The operations further include determining whether to provide a refill for the medication during the current scheduled medication refill based on a current count for the medication at the medication dispensing apparatus and the dynamic refill level.

A further embodiment is directed to a computerized system comprising one or more processors and one or more computer storage media storing computer-useable instructions that, when used by the one or more processors, cause the processors to: estimate a quantity of a medication likely needed from a medication dispensing apparatus during a time period until a next scheduled medication refill for the medication dispensing apparatus, the next scheduled medication refill occurring in accordance with a scheduled basis for refilling the medication dispensing apparatus with a plurality of medications; and set a dynamic refill level for the medication based on the quantity of the medication predicted as likely needed, the dynamic refill level for determining whether to refill the medication during a current scheduled medication refill for the medication dispensing apparatus occurring in accordance with the scheduled basis for refilling the medication dispensing apparatus.

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

The present invention is described in detail below with reference to the attached drawing figures, wherein:

FIGS. 3A and 3B are screen displays showing user interfaces for entering refill parameters for a medication in accordance with an embodiment of the present invention;

DETAILED DESCRIPTION

Figure 1:
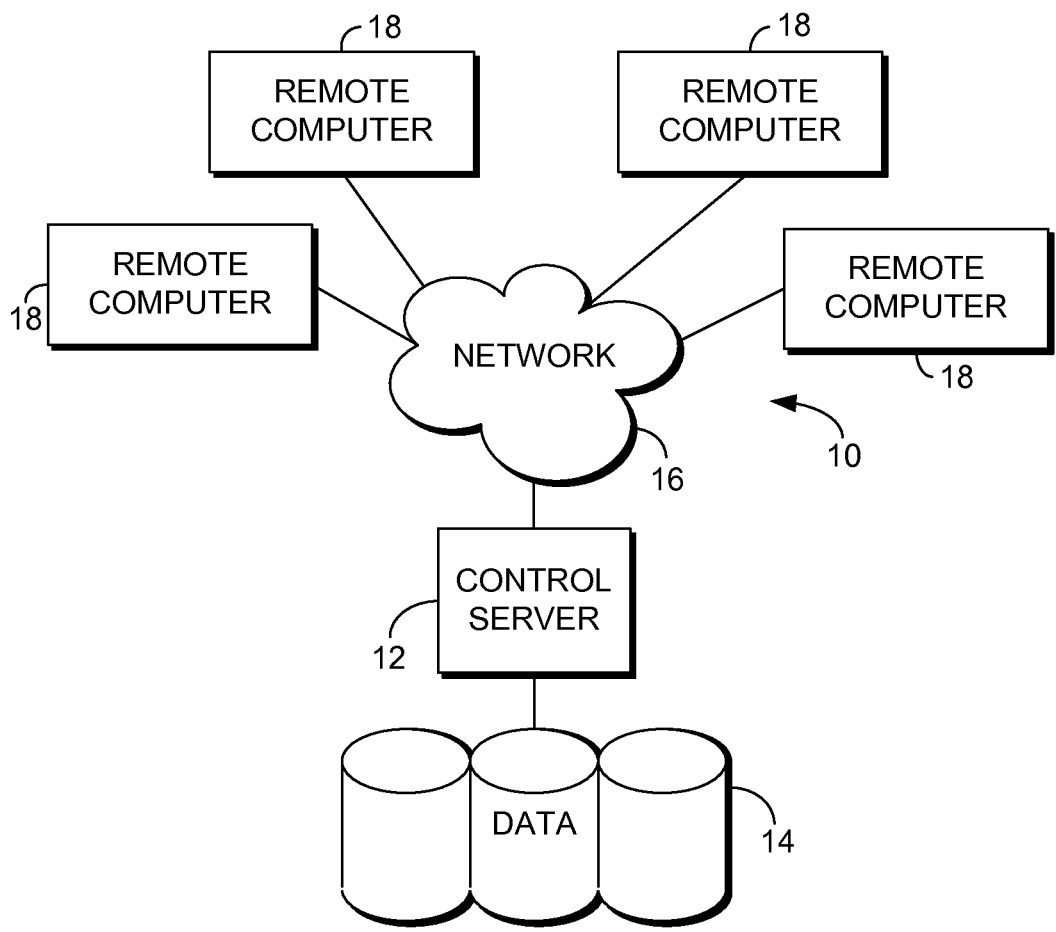
FIG. 1 is a block diagram of an exemplary computing environment suitable for use in implementing the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" may be used herein to connote different components of methods employed, the terms should not be interpreted as implying any particular order among or between various steps herein disclosed unless and except when the order of individual steps is explicitly described.

Embodiments of the present invention are directed to assisting hospital pharmacies to better manage their medication inventories by helping them deliver medications to their medication dispensing apparatuses in a just-in-time manner. As noted above, current approaches to tracking and refilling medication dispensing apparatuses present inefficiencies. In some current approaches, pharmacy department personnel may refill medication dispensing apparatuses on a scheduled basis. Generally, these approaches may include performing a medication refill report process to provide a report that details refill needs for medication dispensing apparatuses. More particularly, the system may maintain a system count for each medication in a medication dispensing apparatus that represents the current quantity of each medication the system believes is stored in the medication dispensing apparatus. The system count for a medication may be updated each time the medication is dispensed such that the system count is kept current. The system may compare the current system count for a medication to a "refill level" for the medication. If the system count for a medication at a medication dispensing apparatus is at or below the refill level, the medication will qualify for refilling and an indication may be provided on a refill report to specify a refill need for the medication at that medication dispensing apparatus.

The refill report is typically provided to the pharmacy department on some scheduled basis (e.g., multiple times a day, daily, every other day, etc.) or when manually requested by pharmacy department personnel. The refill report details the refill needs for medications at medication dispensing apparatuses, and pharmacy department personnel may then fill the medication dispensing apparatuses according to the refill report. In some instances, a maximum count may be used to quantify refill requirements. In particular, the maximum level for a medication represents an upper limit of how many individual items of a medication will be stored in a medication dispensing apparatus or a compartment of a medication dispensing apparatus. The current refill requirements for a medication may then be determined by subtracting the current system count from the maximum level. For instance, if a medication has a maximum level of 20 and a current system count of 8, a refill requirement of 12 may be indicated for the medication.

In addition to the scheduled refill process using a refill level, some current approaches also employ a critical level. If the system count for a medication at a medication dispensing apparatus falls below the critical level for the medication at any time, an alert is provided to the pharmacy department to indicate that the inventory for the medication at that medication dispensing apparatus needs immediate attention.

Currently, the refill parameters (e.g., refill level, maximum level, and critical level) for a medication can be set and modified by a system user, but the system does not change or manipulate these numbers. In accordance with embodiments of the present invention, the system may be enabled to dynamically establish a refill level for a medication at a medication dispensing apparatus at the time a refill report is run. The dynamic refill level may be determined by predicting or estimating the quantity of the medication likely needed to fulfill orders for the medication dispensed from the medication dispensing apparatus during a time period until a next scheduled medication refill for the medication dispensing apparatus. For instance, suppose a medication dispensing apparatus at a hospital is refilled on a daily basis. When the refill report is run on one day to determine refill needs for that day, the process will estimate the quantity of the medication needed until the refill time the following day.

In some embodiments, the estimation of the quantity of medication needed may be based on current patient orders for the medication that are expected be fulfilled by the medication dispensing apparatus before the next schedule medication refill. The estimation may be based on other factors, such as historical information for the medication and the medication dispensing apparatus, a current number of patients located in an area serviced by the medication dispensing apparatus, medical conditions of those patients, and other known information that may impact usage of the medication during the time period until the next scheduled medication refill for the medication dispensing apparatus.

The current system count for a medication is compared with the dynamic refill level to determine if the medication qualifies for a refill during the current refill time. This enables the system to dynamically adjust the medication refill report to prevent unnecessary refills. This will, in turn, save the pharmacy department both time and money in avoided medication inventory and man-hours needed to restock the automated dispensing apparatus.

Recognizing that the dynamic refill level is based on an estimate and that patient census and orders change, some embodiments employ safeguards to ensure that the medication dispensing apparatus does not run out of medication. In some embodiments, the pharmacy department personnel or authorized clinicians can define a buffer that is used to adjust the estimated usage to allow for increased usage. Additionally, a critical level may be used to send pro-active alerts to the pharmacy department to warn them a compartment is near empty.

By way of specific example to illustrate an embodiment of the present invention, suppose that refill activities for a medication dispensing apparatus at a hospital occurs once per 24 hours. The pharmacy department has initially defined a default refill level for medication "A" such that a refill is requested as part of a refill report process if the system count for the medication is below 8 items. The pharmacy department has also enabled dynamic refill functionality and set a 25% buffer for medication "A." When the refill report process is run for the medication dispensing apparatus, medication "A" currently has a system count of 7 items. Using previous approaches, this would qualify for a refill since the current count (i.e., 7 items) is below the refill level (i.e., 8 items). However, using dynamic refill levels in accordance with embodiments of the present invention, the system may evaluate the predicted usage from the current time until the next scheduled refill takes place the next day. In the present example, suppose the system estimates that only 4 items of medication "A" are needed until the next refill. Applying the 25% buffer, the dynamic refill level may be set at 5 items. Since the current system count of 7 items is greater than the dynamic refill level of 5 items, no refill is scheduled for medication "A" for the medication dispensing apparatus at this time.

It should be understood that the process of determining medication refill needs for medication dispensing apparatuses, including the determination of dynamic refill levels, may be performed at any number of computing devices acting either alone or in a distributed environment, in accordance with various embodiments of the present invention. For instance, the process may be performed at a computing device integral with the medication dispensing apparatus, a computing device located in a central pharmacy, and/or a computing device remote from the central pharmacy. Any and all such variations are contemplated to be within the scope of embodiments of the present invention.

Referring to the drawings in general, and initially to FIG. 1 in particular, an exemplary computing system environment, for instance, a medical information computing system, on which embodiments of the present invention may be implemented is illustrated and designated generally as reference numeral 10. It will be understood and appreciated by those of ordinary skill in the art that the illustrated medical information computing system environment 10 is merely an example of one suitable computing environment and is not intended to suggest any limitation as to the scope of use or functionality of the invention. Neither should the medical information computing system environment 10 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 10 includes a general purpose computing device in the form of a server 12. Components of the server 12 may include, without limitation, a processing unit, internal system memory, and a suitable system bus for coupling various system components, including database cluster 14, with the server 12. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The server 12 typically includes, or has access to, a variety of computer readable media, for instance, database cluster 14. Computer readable media can be any available media that may be accessed by server 12, and includes volatile and nonvolatile media, as well as removable and non-removable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the server 12. Communication media typically embodies computer readable instructions, data structures, program modules, or other data in a modulated data signal, such as a carrier wave or other transport mechanism, and may include any information delivery media. As used herein, the term "modulated data signal" refers to a signal that has one or more of its attributes set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 14, provide storage of computer readable instructions, data structures, program modules, and other data for the server 12.

The server 12 may operate in a computer network 16 using logical connections to one or more remote computers 18. Remote computers 18 may be located at a variety of locations in a medical or research environment, for example, but not limited to, clinical laboratories, hospitals and other inpatient settings, veterinary environments, ambulatory settings, medical billing and financial offices, hospital administration settings, home health care environments, and clinicians' offices. Clinicians may include, but are not limited to, a treating physician or physicians, specialists such as surgeons, radiologists, cardiologists, and oncologists, emergency medical technicians, physicians' assistants, nurse practitioners, nurses, nurses' aides, pharmacists, dieticians, microbiologists, laboratory experts, genetic counselors, researchers, veterinarians, students, and the like. The remote computers 18 may also be physically located in non-traditional medical care environments so that the entire health care community may be capable of integration on the network. The remote computers 18 may be personal computers, servers, routers, network PCs, peer devices, other common network nodes, or the like, and may include some or all of the components described above in relation to the server 12. The devices can be personal digital assistants or other like devices.

Exemplary computer networks 16 may include, without limitation, local area networks (LANs) and/or wide area networks (WANs). Such networking environments are commonplace in offices, enterprise-wide computer networks, intranets, and the Internet. When utilized in a WAN networking environment, the server 12 may include a modem or other means for establishing communications over the WAN, such as the Internet. In a networked environment, program modules or portions thereof may be stored in the server 12, in the database cluster 14, or on any of the remote computers 18. For example, and not by way of limitation, various application programs may reside on the memory associated with any one or more of the remote computers 18. It will be appreciated by those of ordinary skill in the art that the network connections shown are exemplary and other means of establishing a communications link between the computers (e.g., server 12 and remote computers 18) may be utilized.

In operation, a user may enter commands and information into the server 12 or convey the commands and information to the server 12 via one or more of the remote computers 18 through input devices, such as a keyboard, a pointing device (commonly referred to as a mouse), a trackball, or a touch pad. Other input devices may include, without limitation, microphones, satellite dishes, scanners, or the like. Commands and information may also be sent directly from a remote healthcare device to the server 12. In addition to a monitor, the server 12 and/or remote computers 18 may include other peripheral output devices, such as speakers and a printer.

Although many other internal components of the server 12 and the remote computers 18 are not shown, those of ordinary skill in the art will appreciate that such components and their interconnection are well known. Accordingly, additional details concerning the internal construction of the server 12 and the remote computers 18 are not further disclosed herein.

Figure 2:
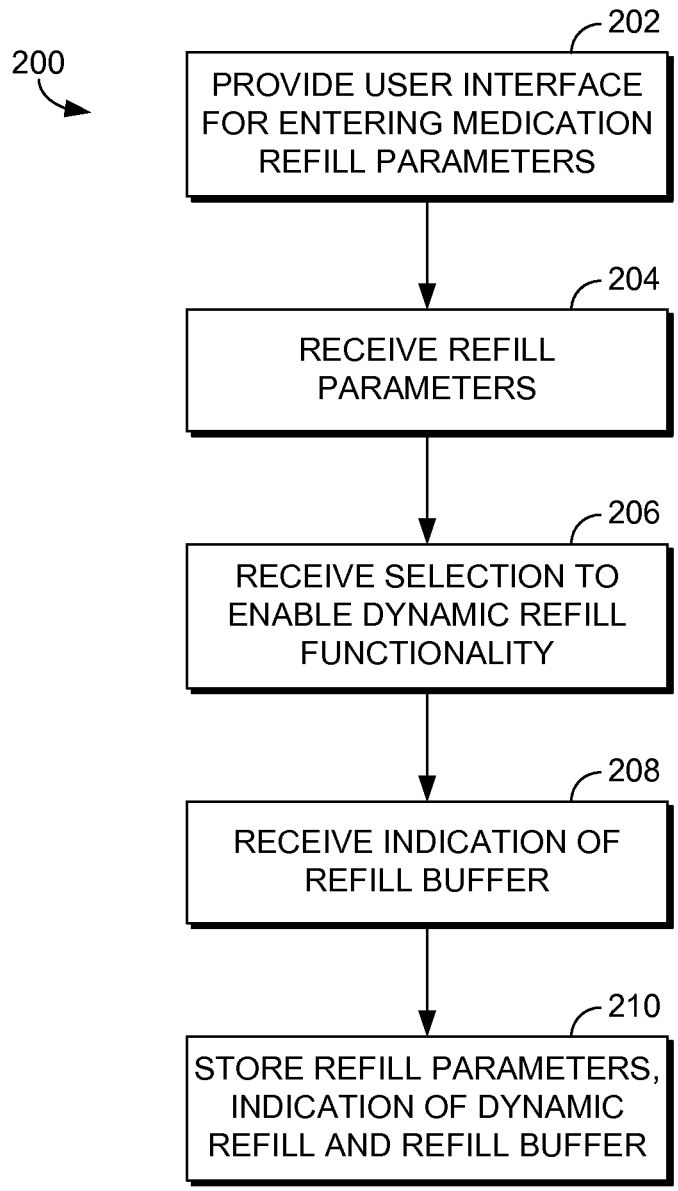
FIG. 2 is a flow diagram showing a method for setting refill parameters for a medication at a medication dispensing apparatus including dynamic refill parameters in accordance with an embodiment of the present invention.

Turning now to FIG. 2, a flow diagram is provided that illustrates a method 200 for setting refill parameters for a medication at a medication dispensing apparatus in accordance with an embodiment of the present invention. As shown at block 202, a user interface for entering medication refill parameters for a particular medication at a particular medication dispensing apparatus is provided. The user interface may be presented to a user via any computing device that is given access to setting medication refill parameters for that medication dispensing apparatus. By way of example only and not limitation, this may include a computing device integral with the medication dispensing apparatus, a computing device located in a central pharmacy, or a computing device remote from the central pharmacy. The user interface may be provided in response to a user command to access refill parameters for a particular medication at a particular medication dispensing apparatus.

Refill parameters for the identified medication and identified medication dispensing apparatus are received via the user interface, as shown at block 204. The refill parameters may include a maximum level, a default refill level, and a critical level for the medication. Other parameters for the medication may also be entered via the user interface. As shown at block 206, a selection to enable dynamic refill functionality for the medication is also received. In addition to receiving the selection to enable dynamic refill functionality, a buffer level is provided for the medication, as shown at block 208. The refill parameters, indication to enable dynamic refill functionality, and buffer level provided for the medication via the user interface is stored, as shown at block 210. The information may be stored locally at the medication dispensing apparatus or remotely at a central database provided at a central pharmacy or another location.

Although the method 200 was discussed in the context of setting the refill parameters for a particular medication at a particular medication dispensing apparatus (i.e., single medication for a single medication dispensing apparatus), it should be understood that similar methods may be employed on a more aggregate level to simultaneously set the refill parameters for multiple different types of medications and/or for multiple different medication dispensing apparatuses. For instance, the refill parameters for a particular type of medication may be simultaneously set for a number of medication dispensing apparatuses containing that type of medication. As another example, the refill parameters for various types of medications in a medication dispensing apparatus may be simultaneously set for that medication dispensing apparatus. As still another example, global refill parameters may be set that apply to all medications at all medication dispensing apparatuses within a healthcare facility. Any and all such variations are contemplated to be within the scope of embodiments of the present invention.

FIGS. 3A and 3B illustrate example screen shots showing user interfaces for entering refill parameters for a medication. It will be understood and appreciated by those of ordinary skill in the art that the screen displays of FIGS. 3A and 3B are provided by way of example only and are not intended to limit the scope of the present invention in any way.

With initial reference to FIG. 3A, a refill parameter user interface is shown for the medication: "Bromanyl 12.5 mg-10 mg/5 mL syr." The refill parameter user interface allows a clinician, administrator, or other authorized personnel to set the refill parameters for the indicated medication. The user interface may be associated with a single medication dispensing apparatus, subset of medication dispensing apparatuses, or all medication dispensing apparatuses within a healthcare facility.

As shown in FIG. 3A, the refill parameters includes a refill level (which has been set at 8), a maximum level (which has been set at 20), and a critical level (which has been set at 5). Based on these settings, when the system count in a medication dispensing apparatus is determined during a scheduled refill report process to be below 8 (i.e., the refill level), an indication to refill the medication dispensing apparatus is provided for the medication. Additionally, if the medication falls below 5 (i.e., the critical level) at any time, an indication to refill the medication dispensing apparatus is provided for the medication. The refill amount may be based on the current system count and the maximum level (i.e., 20). For instance, if the system count is currently 6, the refill amount for the medication may be 14 to bring the quantity of the medication to the maximum level of 20.

The refill parameter user interface in FIG. 3A includes a number of additional parameters for the indicated medication. These parameters include: count requirement, package type, cost center, sub account, and override level. Additionally, an option to prevent changes to the refill parameters may be selected by a user with particular privileges to prevent others from changing the refill parameters.

In accordance with embodiments of the present invention, the refill parameter user interface also includes a selectable option to enable dynamic refill. If left unselected, the scheduled refill report process proceeds with refill need determined based on the set refill level. However, if the dynamic refill option is selected, the scheduled refill report process may include determining a dynamic refill level and employ the dynamic refill level to determine whether a refill for the medication is needed as described herein.

As shown in FIG. 3B, the dynamic refill option has been selected. Based on the selection of this option, a buffer level may be entered. As discussed herein, a dynamic refill may be determined by applying the entered buffer level to a predicted quantity of medication needed during a time period until the next scheduled refill. For instance, if a predicted quantity of medication is 4 and the buffer level is set at 25% as shown in FIG. 3B, the dynamic refill level would be set at 5. In various embodiments of the present invention, a user may enter any value for the buffer or may select from a number of predetermined buffer options. In some instances, the buffer may be set to zero or left blank if no buffer is desired.

After a medication dispensing apparatus has been filled with medications and refill parameters set for the medications, a medication refill report process may be initiated according to some schedule set for the medication dispensing apparatus or in response to a manual trigger from pharmacy department personnel. For instance, depending on medication usage at a medication dispensing apparatus, the medication refill report process may be run two or more times a day, once a day, or on some other schedule. The medication refill report process provides a refill report that details whether any medication refills are required for the medication dispensing apparatus based on current system counts and refill parameters set for the various medications.

Figure 4:
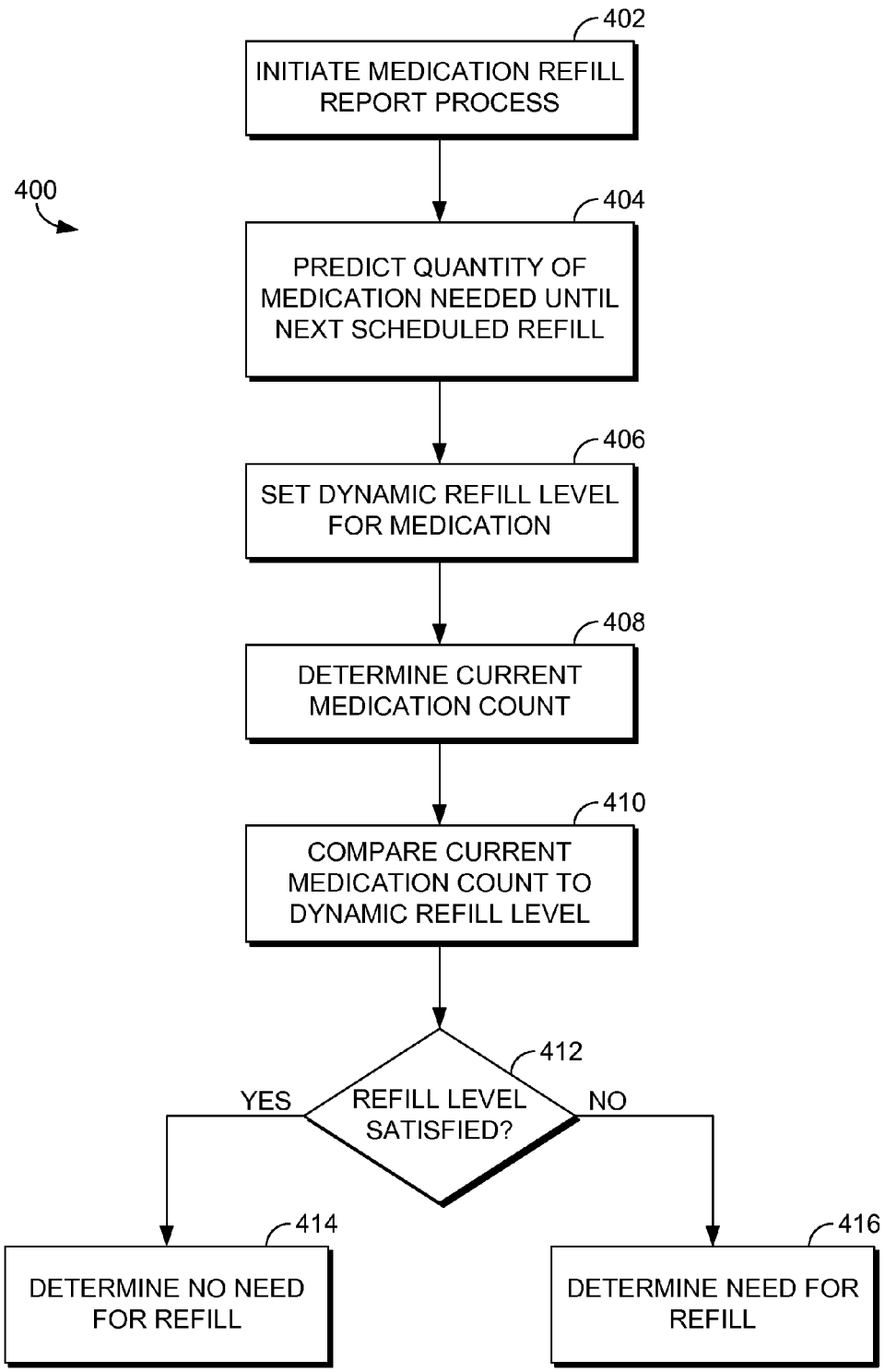
FIG. 4 is a flow diagram showing a method for setting a dynamic refill level for a medication and using the dynamic refill level to determine if a medication refill is needed in accordance with an embodiment of the present invention.

In accordance with embodiments of the present invention, dynamic refill levels may be identified for certain medications and employed to determine whether a refill is required for each of those medications. With reference now to FIG. 4, a flow diagram is provided that illustrates a method 400 for setting a dynamic refill level for a medication and using the dynamic refill level to determine if a medication refill is needed in accordance with an embodiment of the present invention. As shown at block 402, a medication refill report process is initiated for a particular medication dispensing apparatus to provide a report that details medication refill needs. As noted above, this report process may be triggered on some scheduled basis (several times a time, once a day, etc.) or may be manually triggered by pharmacy department personnel.

For a given medication in the medication dispensing apparatus, a quantity of that medication needed until a next scheduled medication refill is predicted, as shown at block 404. This quantity may be predicted based on current orders for the medication expected to be filled by the medication dispensing apparatus. The quantity may also be predicted based on historical information for the medication and/or the medication dispensing apparatus. The predicted quantity may also take into account the current number of patients located in an area serviced by the medication dispensing apparatus, medical conditions of those patients, and other known information that may impact usage of the medication during the time period.

A dynamic refill level for the medication is set based on the predicted quantity, as shown at block 406. In some embodiments, the dynamic refill level may simply correspond with the predicted quantity; while in other embodiments, the dynamic refill level may be set by applying a buffer level to the predicted quantity.

A current system count for the medication in the medication dispensing apparatus is determined, as shown at block 408. The current system count is compared to the dynamic refill level, as shown at block 410. Based on the comparison, a determination is made at block 412 regarding whether the current system count satisfies the dynamic refill level. The current system count may satisfy the dynamic refill level if the current system count is more than the dynamic refill level, equal to or more than the dynamic refill level, or according to some other basis. If the current system count satisfies the dynamic refill level, no need to refill the medication is determined, as shown at block 414. Alternatively, if the current system count does not satisfy the dynamic refill level, a need to refill the medication is determined, as shown at block 416. A notice may be provided to pharmacy personnel to indicate that a refill is required for the medication at the medication dispensing apparatus. This may be provided, for instance, via a medication refill report that indicates medication refill needs for a given medication dispensing apparatus, medication dispensing apparatuses within a particular area of a hospital, or all medication dispensing apparatuses within the hospital.

Although the method 400 was described with reference to a single medication at a single medication dispensing apparatus, it should be understood that when a medication refill report is triggered, a similar dynamic refill determination may be employed for each medication having dynamic refill functionality enabled.

Figure 5:
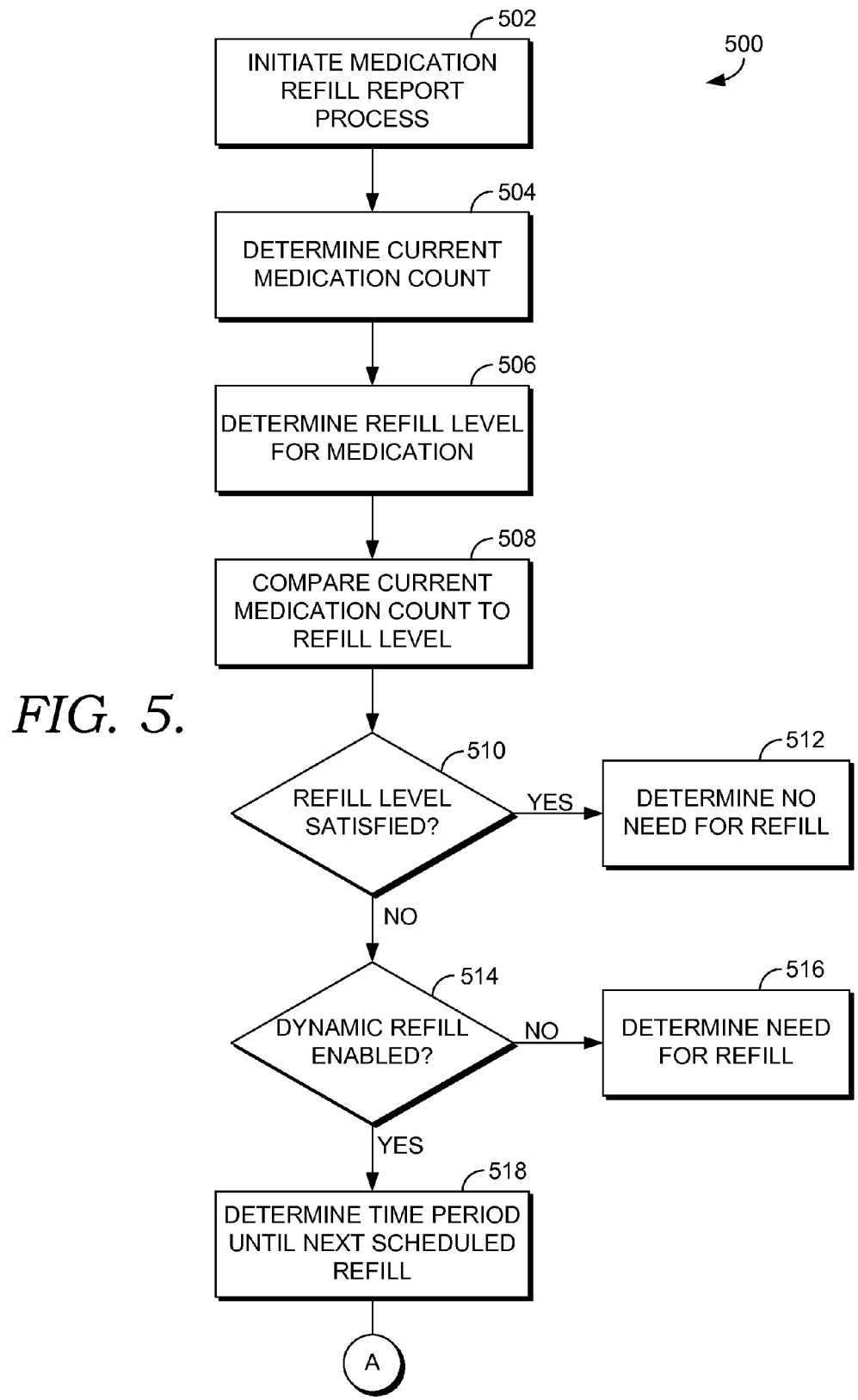
FIG. 5 is a flow diagram showing a method for employing a dynamic refill level in determining whether to refill a medication in accordance with another embodiment of the present invention.
Figure 5:
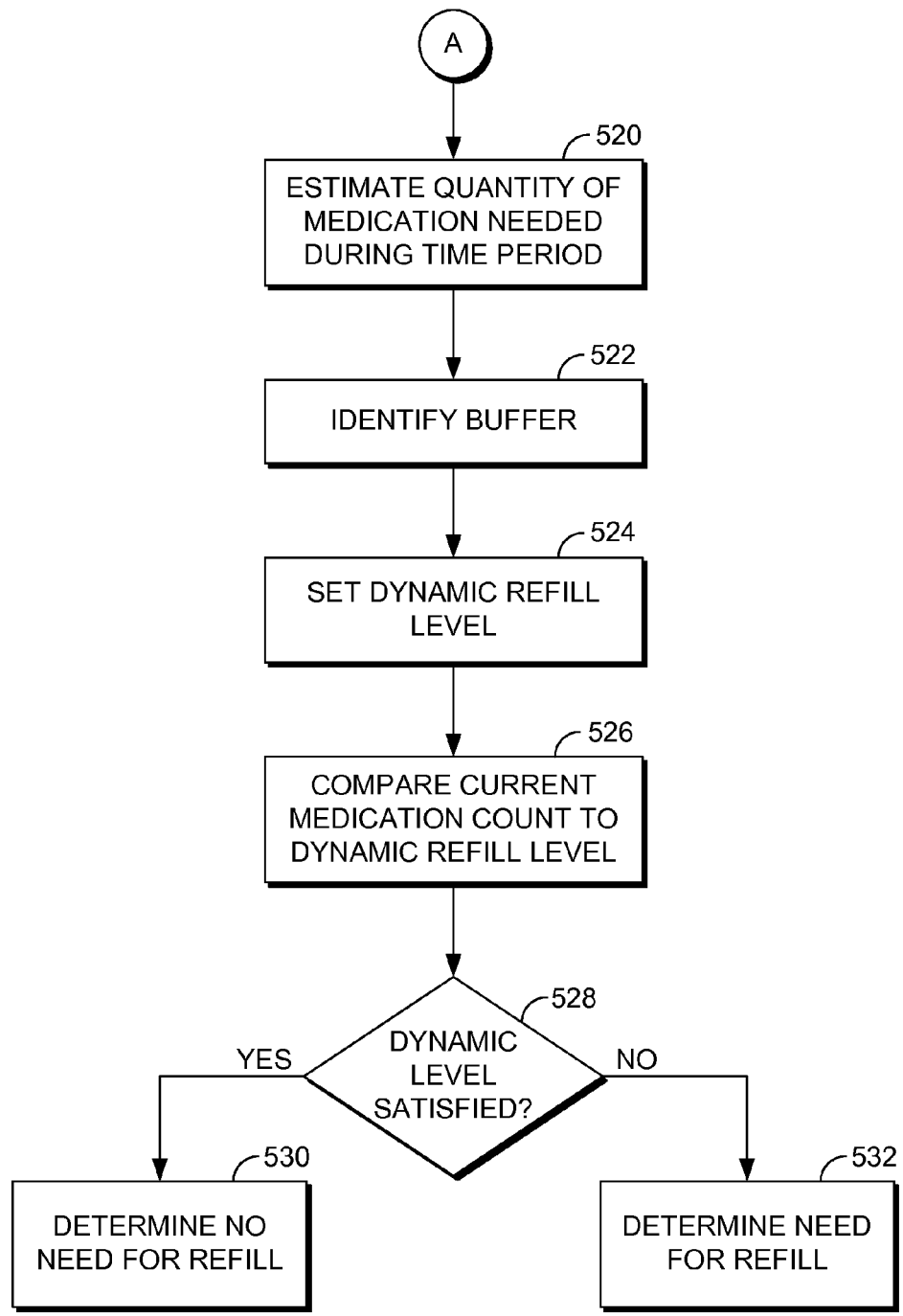

Turning now to FIG. 5, a flow diagram is provided that illustrates a method 500 for employing a dynamic refill level in determining whether to refill a medication in accordance with another embodiment of the present invention. As shown at block 502, a medication refill report process is initiated for a medication dispensing apparatus. This process may be initiated according to some automatic schedule or may be manually triggered by pharmacy department personnel.

A current system count for a particular medication in the medication dispensing apparatus is determined, as shown at block 504. Additionally, a refill level is determined for the medication, as shown at block 506. The refill level may be accessed, for instance, from a refill parameter profile stored for the medication and/or medication dispensing apparatus.

The current system count is compared to the refill level for the medication, as shown at block 508, and a determination is made at block 510 regarding whether the current system count satisfies the refill level. The current system count may satisfy the refill level if the current system count is more than the refill level, equal to or more than the refill level, or according to some other basis. If the current system count satisfies the refill level, no need to refill the medication is determined at block 512, and the process ends. Alternatively, if the current system count does not satisfy the refill level, it is determined at block 514 whether a dynamic refill option has been enabled for this medication and/or medication dispensing apparatus. If a dynamic refill option has not been enabled, a need to refill the medication is determined at block 516, and the process ends. Alternatively, if the dynamic refill option is enabled, the process continues by determining a dynamic refill level for the medication.

As shown at block 518, a time period until a next scheduled refill for the medication dispensing apparatus is determined. In some embodiments, the next scheduled refill may be considered to correspond with the next scheduled medication refill report process. A quantity of the medication needed during that time period is estimated, as shown at block 520. In some embodiments, this estimation may be based on current orders for the medication expected to be filled by the medication dispensing apparatus during the time period. Any order for the medication that is not expected to be filled by that particular medication dispensing apparatus and/or within the determined time period may be ignored. In some embodiments, the estimation of the quantity of medication needed may be based on historical information available for the medication and/or medication dispensing apparatus. The estimation may also take into account the current number of patients located in an area serviced by the medication dispensing apparatus, medical conditions of those patients, and other known information that may impact usage of the medication during the time period.

A buffer level for the medication and/or medication dispensing apparatus is determined, as shown at block 522. The buffer level may be accessed, for instance, from a refill parameter profile stored for the medication and/or medication dispensing apparatus. As shown at block 524, a dynamic refill level is set by applying the buffer level to the quantity of medication estimated to be needed during the time period until the next scheduled refill.

The current system count is compared to the dynamic refill level, as shown at block 526, and a determination is made at block 528 regarding whether the current system count satisfies the dynamic refill level. The current system count may satisfy the dynamic refill level if the current system count is more than the dynamic refill level, equal to or more than the dynamic refill level, or according to some other basis. If the current system count satisfies the dynamic refill level, no need to refill the medication is determined, as shown at block 530. Alternatively, if the current system count does not satisfy the dynamic refill level, a need to refill the medication is determined, as shown at block 532.

In some embodiments, the dynamic refill level determined may be set as the default refill level for the next scheduled refill report process. Alternatively, the default refill level may remain constant. For instance, a user-set refill level may remain the default refill level for each scheduled refill report process.

As can be understood, the present invention provides for determination of dynamic refill levels for medications and determining refill needs for medication dispensing apparatuses based on the dynamical refill levels. The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and subcombinations are of utility and may be employed without reference to other features and subcombinations. This is contemplated and within the scope of the claims.

What is claimed is:

1. One or more computer storage media storing computer-useable instructions that, when used by one or more computing devices, cause the one or more computing devices to perform operations comprising:
   estimating a quantity of a medication likely needed from a medication dispensing apparatus during a time period until a next scheduled medication refill for the medication dispensing apparatus, the next scheduled medication refill occurring in accordance with a scheduled basis for refilling the medication dispensing apparatus with a plurality of medications; and
   setting a dynamic refill level for the medication based on the quantity of the medication predicted as likely needed, the dynamic refill level for determining whether to refill the medication during a current scheduled medication refill for the medication dispensing apparatus occurring in accordance with the scheduled basis for refilling the medication dispensing apparatus.

2. The one or more computer storage media of claim 1, wherein the operations further comprise determining whether to provide a refill for the medication during the current scheduled medication refill based on a current count for the medication at the medication dispensing apparatus and the dynamic refill level.

3. The one or more computer storage media of claim 1, wherein the dynamic refill level is set for the medication based on a medication refill reporting process that is automatically triggered according to the scheduled basis.

4. The one or more computer storage media of claim 1, wherein the quantity of medication likely needed is predicted based on current orders for the medication expected to be filled by the medication dispensing apparatus during the time period until the next scheduled medication refill for the medication dispensing apparatus.

5. The one or more computer storage media of claim 1, wherein the quantity of medication likely needed is predicted based on historical information for at least one selected from the following: the medication and the medication dispensing apparatus.

6. The one or more computer storage media of claim 1, wherein the quantity of medication likely needed is predicted based on a current number of patients located in an area serviced by the medication dispensing apparatus, medical conditions of those patients, and other known information that may impact usage of the medication during the time period until the next scheduled medication refill for the medication dispensing apparatus.

7. The one or more computer storage media of claim 1, wherein the dynamic refill level for the medication is set by applying a buffer level to the quantity of the medication predicted as likely needed.

8. The one or more computer storage media of claim 1, wherein the method further comprises setting the dynamic refill level as a new default refill level used for the medication during the next scheduled medication refill for the medication dispensing apparatus.

9. One or more computer storage media storing computer-useable instructions that, when used by one or more computing devices, cause the one or more computing devices to perform operations comprising:
   determining a dynamic refill level for a medication at a medication dispensing apparatus for a current scheduled medication refill occurring in accordance with a scheduled basis for refilling the medication dispensing apparatus with a plurality of medications, the dynamic refill level being determined by:
   predicting a quantity of the medication likely needed from the medication dispensing apparatus during a time period until a next scheduled medication refill for the medication dispensing apparatus, the next scheduled medication refill occurring in accordance with the scheduled basis for refilling the medication dispensing apparatus, and
   setting the dynamic refill level for the medication based on the quantity of the medication predicted as likely needed; and
   determining whether to provide a refill for the medication during the current scheduled medication refill based on a current count for the medication at the medication dispensing apparatus and the dynamic refill level.

10. The one or more computer storage media of claim 9, wherein the quantity of medication likely needed is predicted based on current orders for the medication expected to be filled by the medication dispensing apparatus during the time period until the next scheduled medication refill for the medication dispensing apparatus.

11. The one or more computer storage media of claim 9, wherein the quantity of medication likely needed is predicted based on historical information for at least one selected from the following: the medication and the medication dispensing apparatus.

12. The one or more computer storage media of claim 9, wherein the quantity of medication likely needed is predicted based on a current number of patients located in an area serviced by the medication dispensing apparatus, medical conditions of those patients, and other known information that may impact usage of the medication during the time period until the next scheduled medication refill for the medication dispensing apparatus.

13. A computerized system comprising:
 one or more processors; and
 one or more computer storage media storing computer-useable instructions that, when used by the one or more processors, cause the processors to:
 estimate a quantity of a medication likely needed from a medication dispensing apparatus during a time period until a next scheduled medication refill for the medication dispensing apparatus, the next scheduled medication refill occurring in accordance with a scheduled basis for refilling the medication dispensing apparatus with a plurality of medications; and
 set a dynamic refill level for the medication based on the quantity of the medication predicted as likely needed, the dynamic refill level for determining whether to refill the medication during a current scheduled medication refill for the medication dispensing apparatus occurring in accordance with the scheduled basis for refilling the medication dispensing apparatus.

14. The system of claim 13, wherein the instructions further comprise operations to determine whether to provide a refill for the medication during the current scheduled medication refill based on a current count for the medication at the medication dispensing apparatus and the dynamic refill level.

15. The system of claim 13, wherein the dynamic refill level is set for the medication based on a medication refill reporting process that is automatically triggered according to the scheduled basis.

16. The system of claim 13, wherein the quantity of medication likely needed is predicted based on current orders for the medication expected to be filled by the medication dispensing apparatus during the time period until the next scheduled medication refill for the medication dispensing apparatus.

17. The system of claim 13, wherein the quantity of medication likely needed is predicted based on historical information for at least one selected from the following: the medication and the medication dispensing apparatus.

18. The system of claim 13, wherein the quantity of medication likely needed is predicted based on a current number of patients located in an area serviced by the medication dispensing apparatus, medical conditions of those patients, and other known information that may impact usage of the medication during the time period until the next scheduled medication refill for the medication dispensing apparatus.

19. The system of claim 13, wherein the dynamic refill level for the medication is set by applying a buffer level to the quantity of the medication predicted as likely needed.

20. The system of claim 13, wherein the instructions further comprise operations to set the dynamic refill level as a new default refill level used for the medication during the next scheduled medication refill for the medication dispensing apparatus.

* * * * *